United States Patent [19]

Steinkamp

[11] Patent Number: 5,270,548
[45] Date of Patent: Dec. 14, 1993

[54] PHASE-SENSITIVE FLOW CYTOMETER

[75] Inventor: John A. Steinkamp, Los Alamos, N. Mex.

[73] Assignee: The United States of America as represented by the United States Department of Energy, Washington, D.C.

[21] Appl. No.: 922,841

[22] Filed: Jul. 31, 1992

[51] Int. Cl.⁵ ............................................. G01N 21/64
[52] U.S. Cl. .............................. 250/461.2; 250/458.1; 250/461.1
[58] Field of Search ............... 250/459.1, 461.2, 458.1, 250/461.1, 302

[56] References Cited

U.S. PATENT DOCUMENTS

| | | | |
|---|---|---|---|
| 3,527,538 | 9/1970 | Allen et al. | 250/458.1 X |
| 4,365,153 | 12/1982 | Seigel et al. | 250/459.1 X |
| 4,573,796 | 3/1986 | Martin et al. | 250/461.2 X |
| 4,609,286 | 9/1986 | Sage, Jr. | 250/461.2 X |
| 4,745,285 | 5/1988 | Recktenwald et al. | 250/461.2 X |
| 5,185,265 | 2/1993 | Steen et al. | 250/459.1 X |
| 5,196,709 | 3/1993 | Berndt et al. | 250/458.1 |

OTHER PUBLICATIONS

T. V. Veselova, "Fluorometric Method for Individual Recording of Spectra in Systems Containing Two Types of Luminescent Centers," 29 Opt. Spectrosc, pp. 617–618 (1970).
M. R. Loken et al., "Two-Color Immunofluorescence Using a Fluorescence-Activated Cell Sorter," 25 J. Histochem. Cytochem. (7), pp. 899–907 (1977).
D. M. Jameson et al., "The Measurement and Analysis of Heterogeneous Emissions by Multifrequency Phase and Modulation Fluorometry," 20 Appl. Spectroscopy Rev. (1), pp. 55–106 (1984).
L. B. McGown et al., "Phase-Resolved Fluoresence Spectroscopy," 56 Anal. Chem. (13), pp. 1400A–1415A.
J. A. Steinkamp et al., "Improved Multilaser/Multi-parameter Flow Cytometer for Analysis and Sorting of Cells and Particles," 62 Rev. Sci. Instrum. (11), pp. 2751–2764 (Nov. 1991).

Primary Examiner—Constantine Hannaher
Assistant Examiner—Edward J. Glick
Attorney, Agent, or Firm—Ray G. Wilson; Paul D. Gaetjens; William R. Moser

[57] ABSTRACT

A phase-sensitive flow cytometer (FCM) provides additional FCM capability to use the fluorescence lifetime of one or more fluorochromes bound to single cells to provide additional information regarding the cells. The resulting fluorescence emission can be resolved into individual fluorescence signals if two fluorochromes are present or can be converted directly to a decay lifetime from a single fluorochrome. The excitation light for the fluorochromes is modulated to produce an amplitude modulated fluorescence pulse as the fluorochrome is excited in the FCM. The modulation signal also forms a reference signal that is phase-shifted a selected amount for subsequent mixing with the output modulated fluorescence intensity signal in phase-sensitive detection circuitry. The output from the phase-sensitive circuitry is then an individual resolved fluorochrome signal or a single fluorochrome decay lifetime, depending on the applied phase shifts.

4 Claims, 6 Drawing Sheets

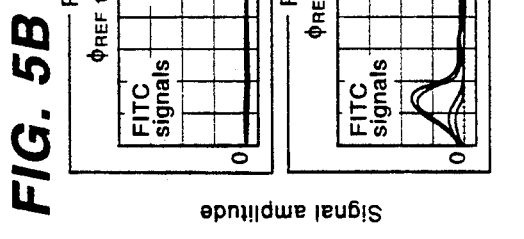
FIG. 5A
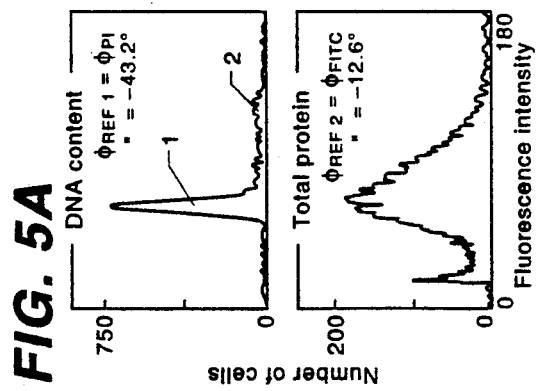
FIG. 5B
FIG. 5C
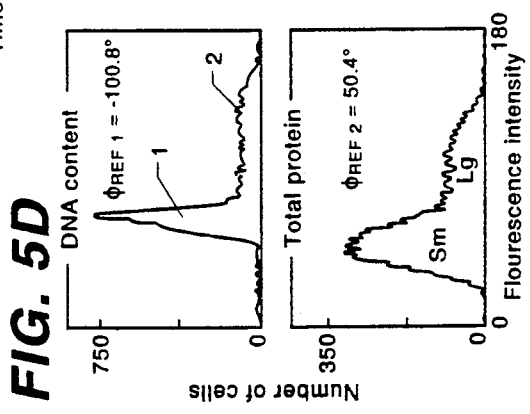
FIG. 5D
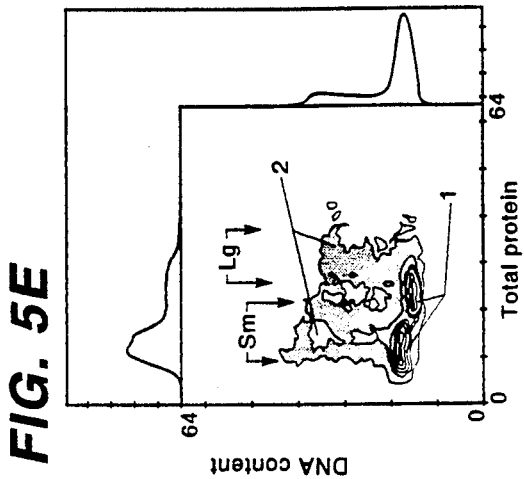
FIG. 5E
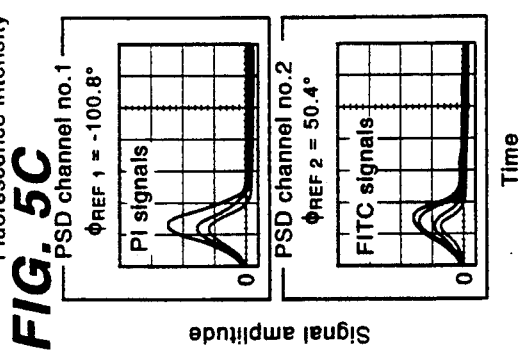

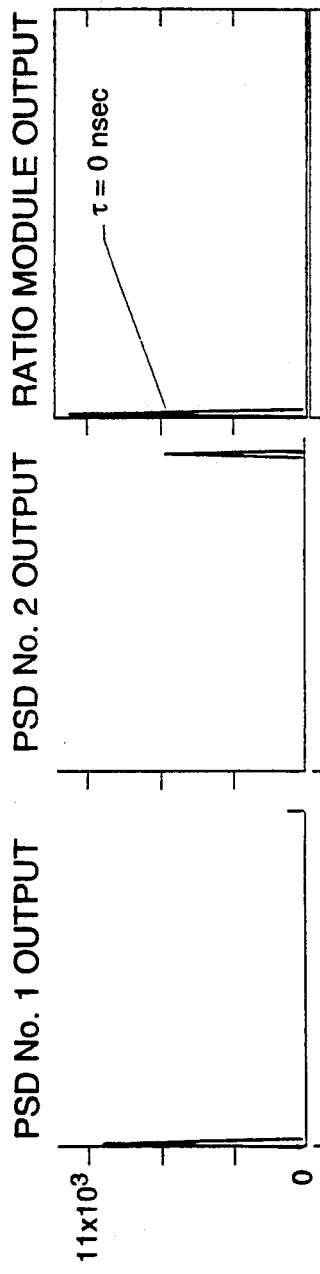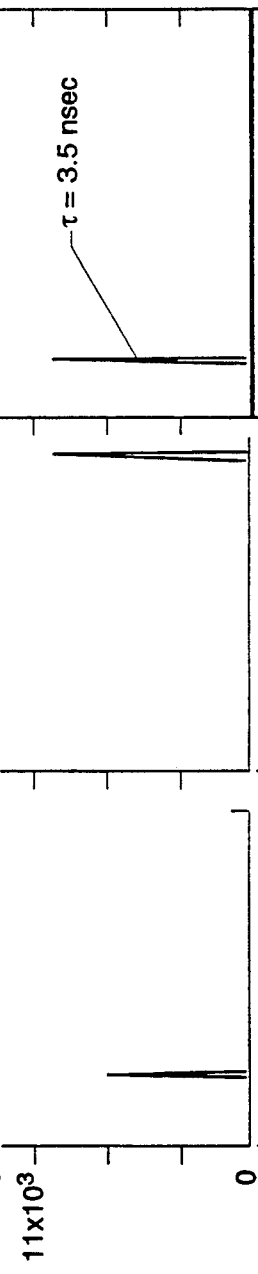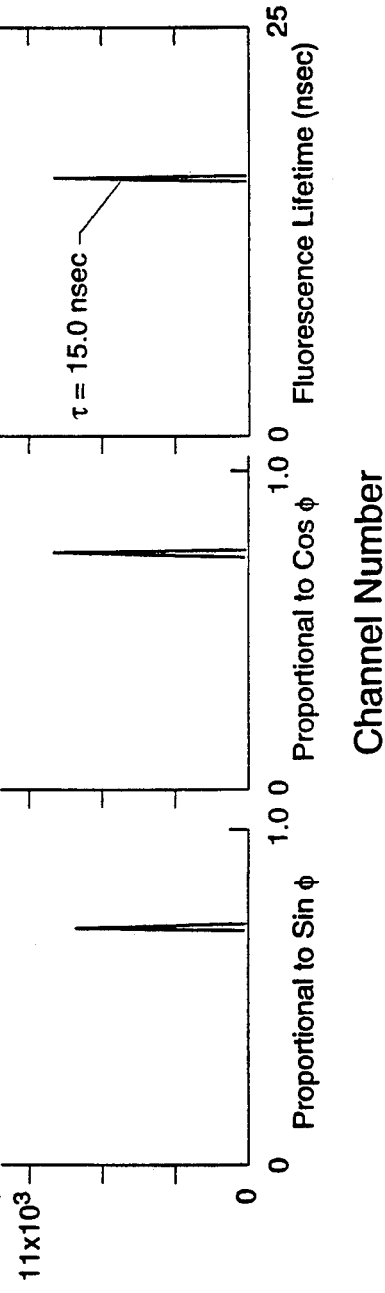
FIG. 6A
FIG. 6B
FIG. 6C

PHASE-SENSITIVE FLOW CYTOMETER

This invention is the result of a contract with the Department of Energy (Contract No. W-7405-ENG-36).

BACKGROUND OF THE INVENTION

This invention relates to flow cytometry and, more particularly, to flow cytometers for processing fluorescence emissions by lifetime-induced phase shifts.

Flow cytometry (FCM) is an important analytical tool for detecting characteristic fluorescence emission intensities from cellular components such as DNA, RNA, proteins, enzymes, and lipids stained with fluorescent dyes, antigenic determinants labeled with antibodies conjugated to fluorochrome, hybridized DNA sequences labeled with fluorescent probes, and the like, measured on a cell-by-cell basis at high speed. Fluorescence emission characteristics are detected, such as fluorescence signal intensity, signal width, and area, within specified wavelength regions defined by the fluorescence spectra as cells/particles intersect a cw laser or arc lamp excitation source. Conventional FCM has become an important clinical diagnostic and biomedical research tool, demanding ever-expanding capabilities to meet clinical and research needs. For example, the labeling of particles and cells with multiple fluorochromes is often required to provide a correlated analysis of cellular properties.

A major limitation of FCM is the availability of fluorescent dyes with common excitation regions, i.e., a single excitation source, with a resulting emission spectra that are sufficiently separated to permit measurement by multi-color detection methods. Examples of fluorochromes having overlapping emission spectra are shown in Table A. Fluorescence signal compensation using differential amplifiers, as described by Loken et al. 25 J. Histochem. and Cytochem. 899 (1977), has been employed to separate signals resulting from overlapping emission spectra in FCM applications, but with a loss in signal intensity depending upon the amount of "electronic compensation" needed to resolve the two signals.

TABLE A

| LASER EXCITATION WAVELENGTH (nm) | FLUORESCENT STAINS |
| --- | --- |
| UV | Hoechst 33342, DAPI, DIPI, ANSA, DANSYL, NADPH, $Ca^{++}$ Indicators, Coumarins |
| 413 | Brilliant Sulfaflavine, Fluorescamine, Mithramycin, Chromomycin |
| 457 | Mithramycin, Chromomycin, Acriflavine, FITC, FDA, Acridine Orange |
| 488/514 | Acriflavine, Acridine Orange, FITC, FDA, Rhodamine 123, Ethidium Bromide, Propidium Iodide, Phycoerythrin, Nile Red, SNARF-1 |
| 528/530 | Phycoerythrin, Phyronin Y, TmRITC, Rhodamine B and 3G, Nile Red, Resorufin, SNARF-1 |
| 568 | Texas Red, XRITC, Rhodamine 640, L. Rhodamine, Oxadicarbocyanin, Allophycocyanin |

Another approach has used multiple excitation wavelengths to sequentially excite cells that are labeled with fluorochromes having separated excitation spectra that are sequentially detected on discrete photomultiplier tubes as described in Steinkamp et al., 62 Rev. Sci. Instrum. 2751-2764 (1991). This approach has increased the number of fluorescent dyes suitable for multilabeling experiments, but the instrument hardware has become increasingly complex.

Overlapping fluorescence spectra from batch solutions have been resolved using phase sensitive electronics to discriminate between emissions having different lifetimes, e.g., in spectrofluorometry, as originally described by Veselova, "Fluorometric Method for Individual Recording of Spectra in Systems Containing Two Types of Luminescent Centers," 29 Optics and Spectroscopy 617-618 (1970). Typical applications are described in McGown et al., "Phase-Resolved Fluorescence Spectroscopy," 56 Anal. Chem. No 13, pp. 1400A-1414A (November 1984) and Jameson et al., "The Measurement and Analysis of Heterogeneous Emissions by Multifrequency Phase and Modulation Fluorometry," 20(1) Appl. Spectrosc. Rev., pp. 55-103 (1984).

In accordance with the present invention, phase resolution techniques are applied to FCM to extend the capability of FCM to heterogeneous fluorescence emissions from at least two fluorochromes having overlapping emission (wavelength) spectra, but different fluorescence lifetimes. In addition to providing a new FCM measurement capability, i.e., the ability to resolve fluorochromes having overlapping emission spectra, it is recognized that phase-resolved measurements based on lifetime differences will improve measurement sensitivity, increase analytical resolution, and facilitate the interpretation of flow cytometric data by reducing background interferences from cellular autofluorescence, unbound (free) dye, nonspecific dye-binding, and Raman and Rayleigh scatter.

The ability to determine lifetime information from individual cell fluorescence emissions is also important since fluorescence decay/lifetime parameters provide additional information about fluorochrome/cell interactions. The fluorescence lifetime of dye molecules bound to specific components in cells and particles, such as DNA, can be influenced by local factors near the binding site, such as solvent polarity, energy transfer, excited-state reactions, and quenching. Thus, lifetime measurements add to flow cytometry the capability to probe structures on the molecular level in single cells, e.g. DNA structure.

Accordingly, it is an object of the present invention to use differences in fluorescence decay lifetimes to resolve signals from simultaneous fluorescence emissions having overlapping emission spectra arising from single-frequency excitation in a FCM.

It is another object of the present invention to enable an increased number of fluorochromes to be used for multilabeling experiments.

Yet another object of the present invention is to provide fluorescence decay lifetime as an output parameter from a FCM for use in characterizing fluorochrome/cell binding under a variety of conditions.

Still another object of the present invention is to improve the sensitivity and resolution of a FCM with regard to background interference fluorescence, such as intrinsic cellular autofluorescence, free/unbound dye, nonspecific staining, and Raman and Rayleigh scatter.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as this invention may comprise a phase-sensitive cytometer for resolving fluorescence emissions from fluorochrome labeled cells into two components. A flow cytometer provides a flow stream containing the labeled cells where the labeled cells are excited to fluorescence by an excitation light. A modulator operates to modulate the excitation light and to generate a reference signal at a selected modulation frequency. A detector receives fluorescence emission spectra from the labeled cells that is a modulated signal and outputs a modulated intensity signal functionally related to the fluorescence signal from the labeled cells.

A first phase detector resolves the modulated signal into two signal components, each functionally related to a different one of the two fluorochromes In another embodiment of the present invention, the apparatus comprises a phase-sensitive flow cytometer for determining the fluorescence decay lifetime of a fluorescence emission. A flow cytometer provides a flow stream containing cells labeled with a fluorochrome, where the fluorochrome is excited to fluorescence by an excitation light. A modulator operates to modulate the excitation light and to generate a reference signal at a selected modulation frequency. A detector receives fluorescence spectra from the fluorochrome that is modulated signal and outputs a modulated intensity signal functionally related to the fluorescence spectra from the fluorochrome. A phase detector receives the modulated intensity signal and outputs two phase shifted signals whose ratio is functionally related to the fluorescence decay lifetime.

BRIEF DESCRIPTION OF THE DRAWINGS

The accompanying drawings, which are incorporated in and form a part of the specification, illustrate embodiments of the present invention and, together with the description, serve to explain the principles of the invention. In the drawings:

FIGS. 5A, 5B, 5C, 5D, AND 5E present experimental results from a FCM using phase-sensitive electronics.

FIGS. 6A, 6B, and 6C graphically depicts direct fluorescence lifetime determination using phase-sensitive electronics.

DETAILED DESCRIPTION OF THE INVENTION

The present invention is directed to a phase-sensitive flow cytometer (PSFCM) to resolve signals from simultaneous fluorescence emissions based on differences in decay lifetimes and to quantify single decay lifetimes of cells, subcellular components, chromosomes, and/or particles labeled with fluorescent dyes using single-frequency excitation and homodyne signal processing. As hereinafter described, the PSFCM combines flow cytometry and phase-sensitive fluorescence spectroscopy measurement principles to provide new and unique capabilities for making phase-resolved measurements on single cells in a flow regime.

Figure 1:
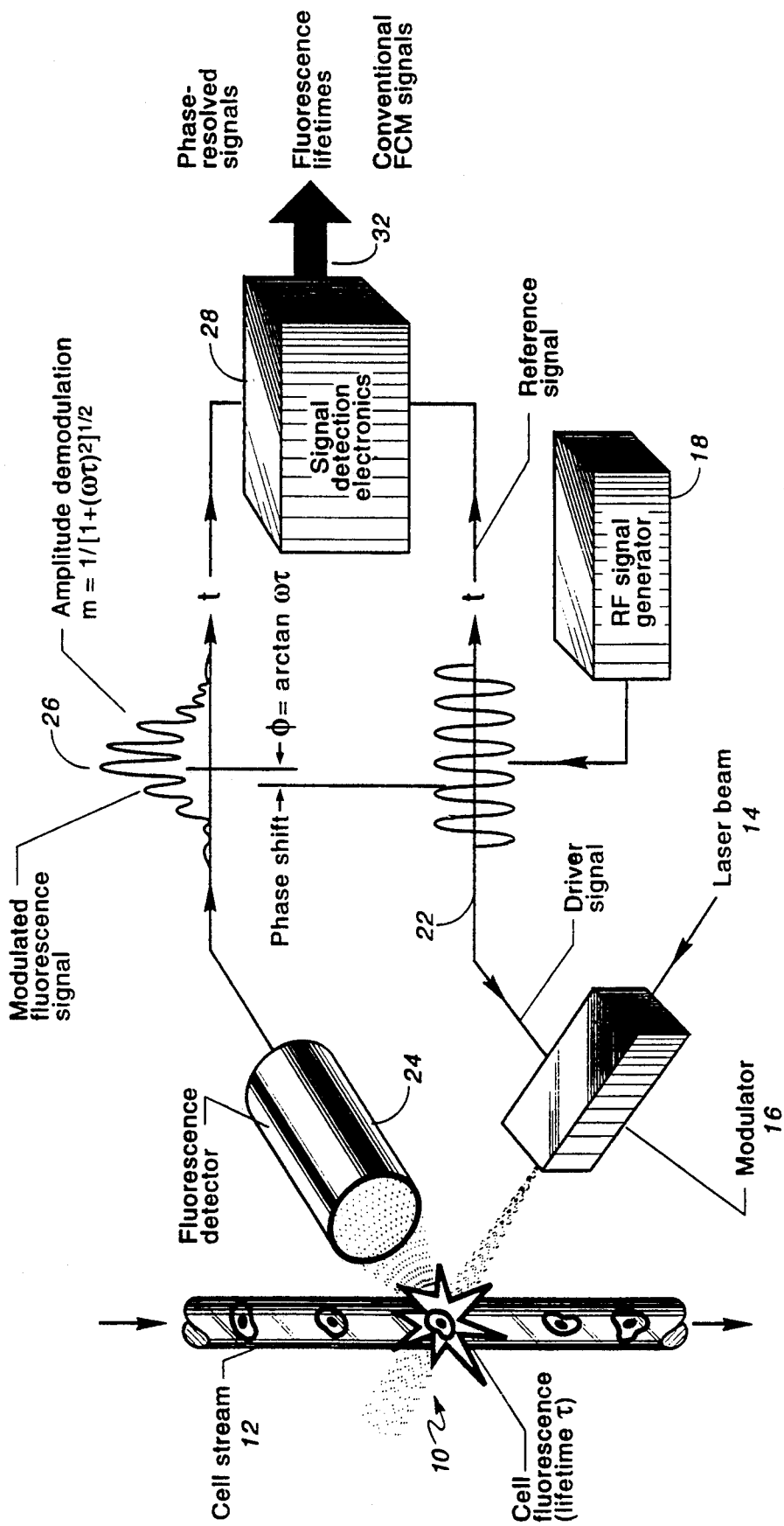
FIG. 1 is a pictorial illustration of one embodiment of the present invention.

FIG. 1 depicts a pictorial illustration of a PSFCM 10 for analyzing a stream of cells or particles 12, i.e., a cell-by-cell analysis as each cell intersects a modulated excitation light. As hereinafter used, the term "cells" will include both cells, chromosomes, and particles that are conventionally analyzed using FCM equipment. Cells in stream 12 are irradiated with laser beam 14 after beam 14 has been modulated by modulator 16 through driver signal 22 produced by rf signal generator 18. The resulting cell fluorescence emission is detected by fluorescence detector 24, conventionally comprising light collection optics, a filter, and a photomultiplier amplifier, which outputs a modulated fluorescence signal 26. Output signal 26 is shifted in phase from modulation reference signal 22 by an amount $$\phi_s = \arctan \omega \tau.$$

The modulation of fluorescence signal 26 is given by $$m_s = [1+(\omega\tau)^2]^{-\frac{1}{2}},$$

where $\tau$ is the fluorescence lifetime and is the frequency of modulator/reference signal 22.

Figure 2A:
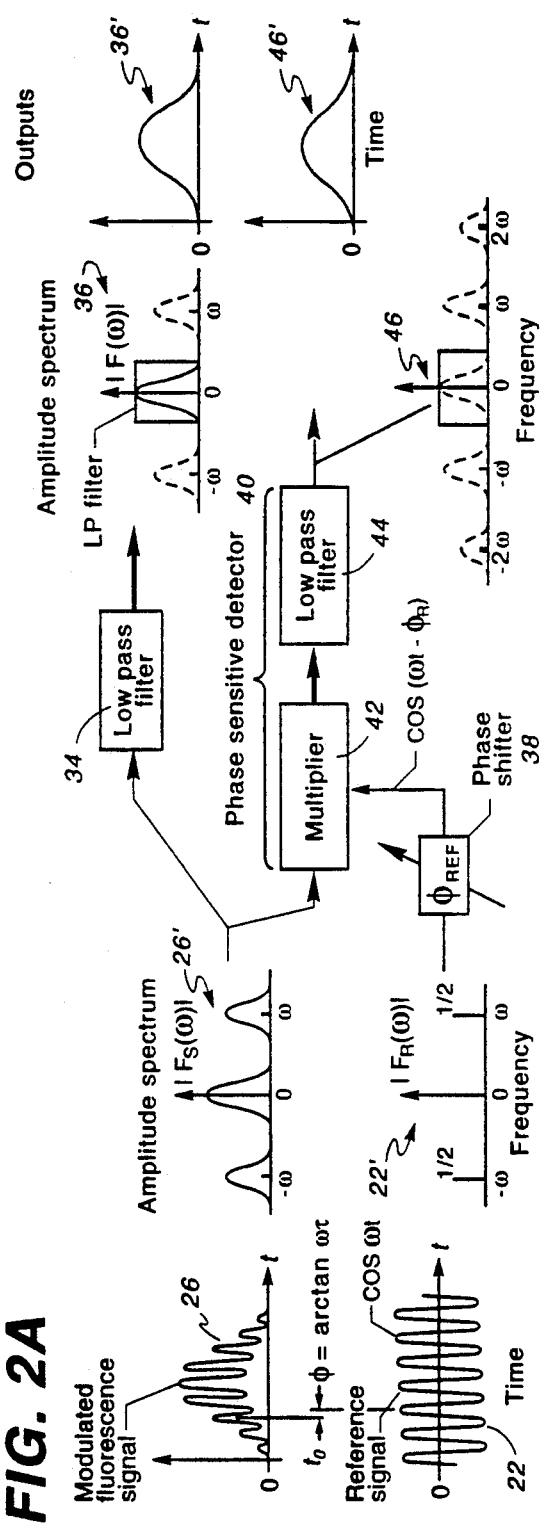
FIGS. 2A and 2B are graphical illustrations of signal processing of the apparatus shown in FIG. 1.

The modulated fluorescence signal 26 is further processed by signal detection electronics 28 to extract output signals 32, comprising phase-resolved, fluorescence lifetime, and conventional FCM fluorescence intensity signals. The signal processing by signal detection electronics 28 is further shown in FIGS. 2A and 2B. FIG. 2A shows modulated fluorescence signal 26 in amplitude vs. time and a corresponding amplitude spectrum 26'. Reference signal 22 is likewise shown in both amplitude vs. time format 22 and amplitude spectrum format 22'. Conventional FCM signals 36 and 36' are obtained by simply passing modulated fluorescence signal 26 through low pass filter 34 to extract only the amplitude, i.e., intensity, information.

Phase and lifetime information in modulated signal 26, 26' is extracted by phase sensitive detection of differences in fluorescence lifetimes. The homodyne signal detection electronics consist of a phase-sensitive detector 40 formed from multiplier 42, phase shifter 38, and low pass filter 44. Phase shifter 38 shifts the phase ($\phi_{ref}$) of the cos $\phi t$ reference signal 22 input to multiplier 42 with respect to modulated fluorescence signal 26. Output signal 46 $v_o(t)$ is a Gaussian-shaped signal obtained by filtering the output of multiplier 42 through low pass filter 44 to remove the fundamental and secondary harmonic frequency components and retain the low frequency components. These low frequency components in filtered signal 46 correspond to the time-dependent output 46' of the phase sensitive detector expressed as $$v_o(t) = V(m/2)\cos(\phi - \phi_{ref})e^{-a^2(t-t_0)^2},$$

where V is a fluorescence intensity, m is a demodulation factor, $\phi$ is the phase shift introduced by the fluorescence decay, a is a term related to the velocity of the cell across the laser beam at time $t_o$, and t is the time.

The principle of phase suppression, as applied to resolving a fluorescence signal having two fluorescence signal components by phase-sensitive detection in flow, is expressed as:

$$v_o(t) = V_1(m_1/2)\cos(\phi_1 - \phi_{ref})e^{-a^2(t-t_o)^2} + V_2(m_2/2)\cos(\phi_2 - \phi_{ref})e^{-a^2(t-t_o)^2}$$

Each of the signal components arises from a different excited fluorochrome lifetime. In order to resolve one signal from the other the reference signal phase is shifted by an amount $\phi_{ref} = -\pi/2 + \phi_2$ or $\phi_{ref} = \pi/2 + \phi_1$. These phase shifts act to null either the first or second signal component, respectively, to yield either $$v_{01}(t) = V_1 m_2/2 \sin(\phi_2 - \phi_1)e^{-a^2(t-t_o)^2}$$

or $$v_{02}(t) = V_2 m_2/2 \sin(\phi_2 - \phi_1)e^{-a^2(t-t_o)^2}$$

Both signal components are resolved, but with a loss in amplitude of $\sin(\phi_2 - \phi_1)$. Thus, a single modulated fluorescence signal from a cell excited during passage through a flow cytometer, can be resolved into two conventional fluorochrome signal components.

Figure 2B:
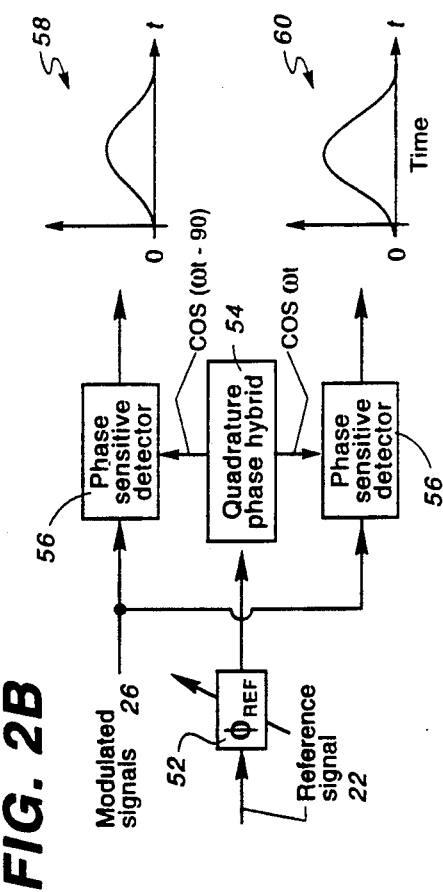

FIG. 2B graphically illustrates signal processing for providing single decay lifetime measurements in flow by a two-phase detector method. Phase sensitive detectors 56 each receive modulated fluorescence signal 26. Reference signal 22 is input through phase shifter 52 to quadrature phase hybrid circuit 54, which outputs reference signal 22 with 0° and 90° phase shifts for input to multipliers in phase sensitive detectors 56. Outputs 58, 60 from detectors 56 are then expressed as $$v_{\phi - 90}(t) = Vm/2(\sin\phi_s)e^{-a^2(t-t_o)^2},$$

and $$v_\phi(t) = Vm/2(\cos\phi_s)e^{-a^2(t-t_o)^2}.$$

These outputs are then ratioed to yield $\tan \phi_s$, where $\phi_s = \arctan \omega\tau$. Thus, the decay lifetime is then expressed as $$\tau = (1/\omega)v_{(\phi-90)}(t)/v_{(\phi)}(t).$$

Figure 3:
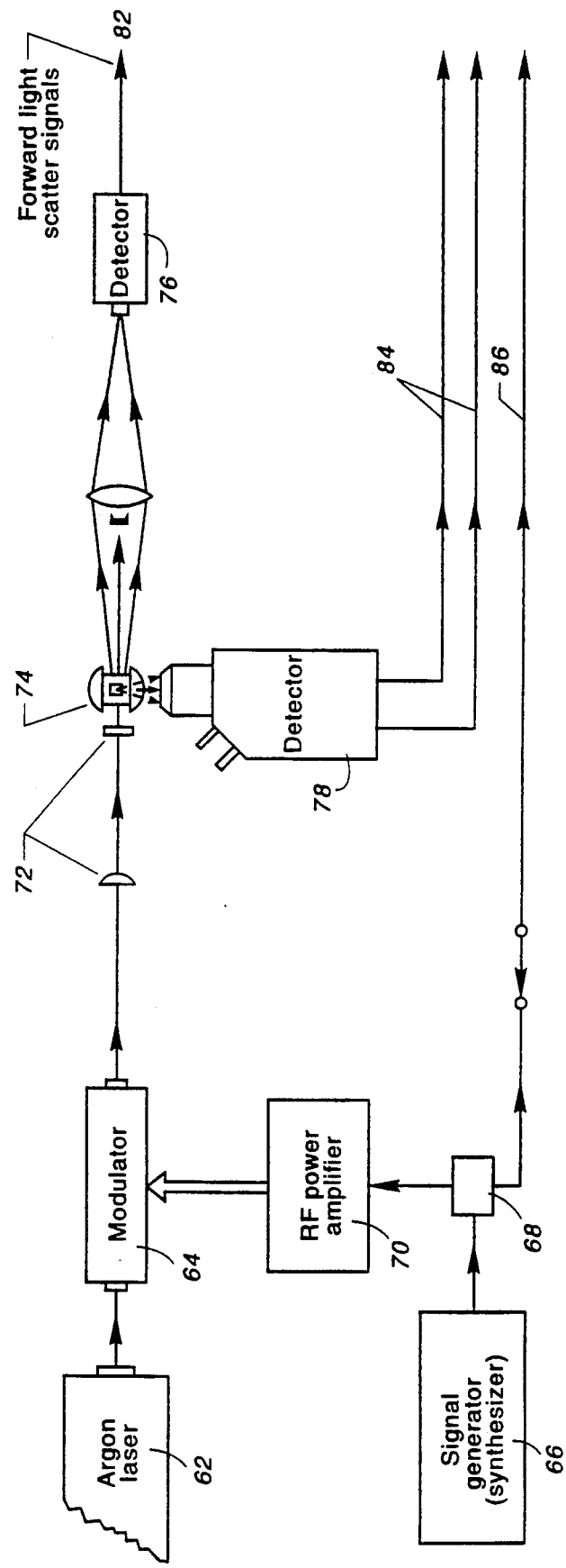
FIG. 3 is a schematic diagram in block diagram form of the apparatus shown in FIG. 1.

Referring now to FIG. 3, there is shown in block diagram form a schematic for a flow cytometer to detect output fluorescence from one or two fluorochromes in accordance with the present invention. Argon laser 62, e.g., a Spectra Physics 5W Model 2025-05 laser, is provided as an excitation source, with an output that is modulated by an electro-optical modulator 64, e.g., a Conoptics Model 50 having a bandwidth of dc-50 MHz. Modulator 64 is conventionally mounted on a precision slide (not shown) for alignment of modulator 64 with the axis of the beam from laser 62 or movement into or out of the laser input beam.

A reference and modulation signal is provided by signal generator 66. e.g., a Hewlett-Packard Model 3335A synthesized sine wave generator with an output range from 200 Hz to 81 MHz. The reference signal output is split by signal splitter 68 for input through RF power amplifier 70 to modulator 64 and for the reference signal described above for phase resolution of output signal components. The output beam from laser 62 has a Gaussian intensity profile and is focused by a pair of quartz cylindrical lenses 72 of focal length 30 cm and 5.4 cm to an elliptical shape for illuminating flow chamber 74. Flow chamber 74 may be a Coulter Corp. Profile "Biosense" flow chamber. In one embodiment, a beam splitter (not shown) may be located between laser 62 and flow chamber 74 to deflect a small portion of the modulated laser beam to a laser monitor.

The fluorescence emitted by cells having fluorochromes excited by modulated laser 62 is detected in a direction orthogonal to the laser beam by fluorescence detector 78 or as conventional forward light scatter (0.5°–2.0°) signals by detector 76 to form forward light scatter signals 82. A suitable forward scatter detection system includes a 10 cm focal length lens placed 20 cm from the laser beam-cell intersection and detector 76 located 20 cm from the collection lens. An obscuration bar may be placed in front of the collection lens to block incident laser illumination from the reaching detector 76.

Detector 78 detects the fluorescence emission or emissions containing lifetime decay information. In one embodiment, the conventional optics are replaced with a F/0.95 CCTV lens from D.O. Optical and one or more a bandwidth of dc-50 MHz. Modulator 64 is photomultiplier tubes. A Corning Glass 3-69 colored glass, long pass filter is located between the lenses to provide a barrier filter to block scattered laser excitation light and pass emitted fluorescence above the 500 nm wavelength cutoff point. Suitable detectors for detector 76 and detector 78 may include Burle Industries 4526 dormer-window 10-stage photomultiplier tubes and Comlinear Corp. Model 401 operational amplifiers (150 MHz bandwidth) configured in the transimpedance mode using 7.5 K ohm feedback resistors. A suitable preamplifier output impedance is 50 ohms. Neutral density filters may be placed in front of the photomultiplier tube photocathodes of detector 76 to limit the tube current.

Figure 4A:
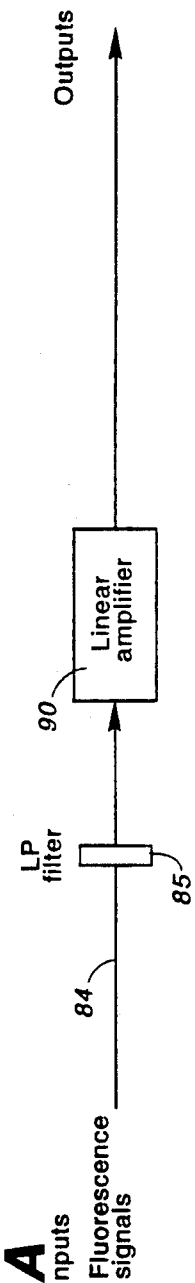
FIGS. 4A, 4B, and 4C are schematic diagrams in block diagram form of electronics for outputting the signals shown in FIG. 2.
Figure 4B:
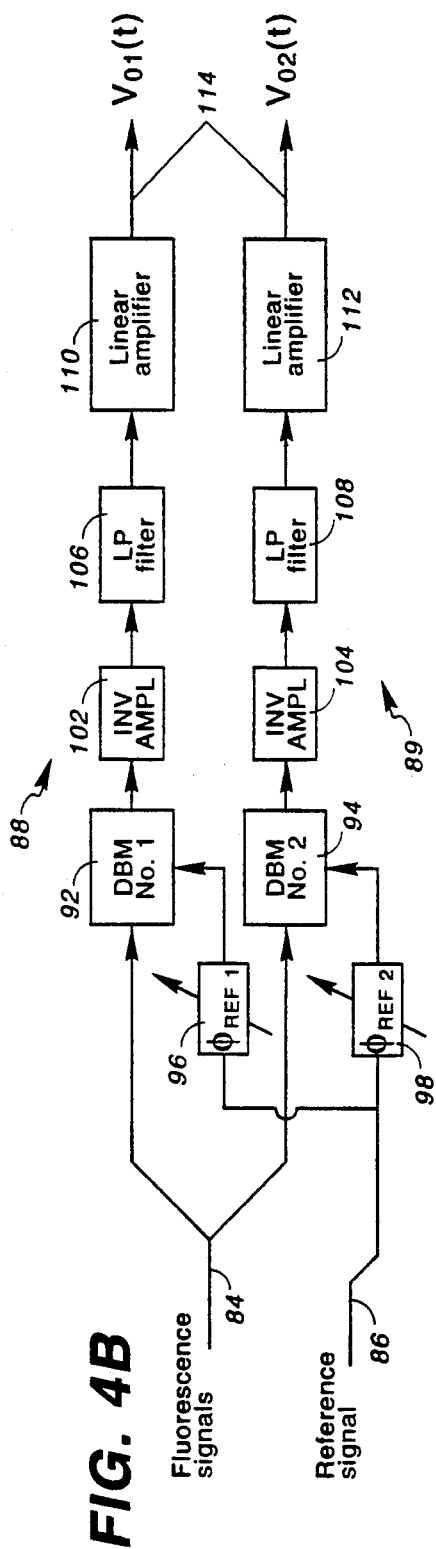
Figure 4C:
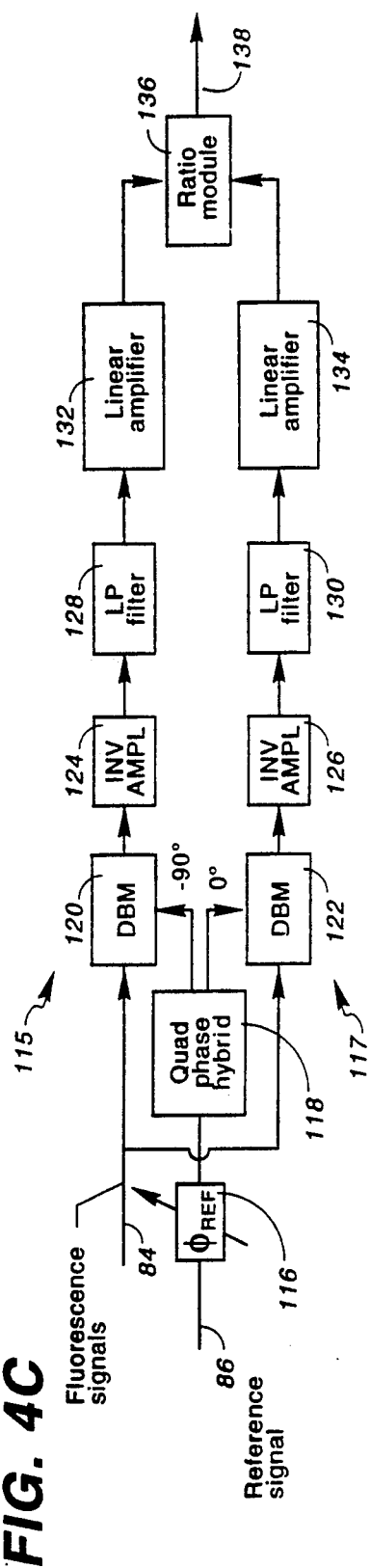

Processing of signal 84, output by detector 78, is done by circuitry shown by block diagram schematics in FIGS. 4A, 4B, and 4C. Fluorescence signal(s) 84 may be input through LP filter 85 to remove the modulation. The demodulated signal is simply amplified by linear amplifier 90, as shown in FIG. 4A, since the information of interest is the conventional fluorescence intensity.

FIG. 4B illustrates processing from a dual channel phase-sensitive detector 78 to resolve fluorescence signals 84 into two components. Each phase sensitive detection channel 88. 89 consists of double balanced mixer/multiplier phase detector 92, 94, such as a Mini-Circuits Model ZRPD-1; inverting amplifiers 102, 104; low-pass filters 106, 108, such as a Krohn-Hite Model 3202 dual-channel electronic filter operating as a 0–160 KHz low-pass filter; and linear amplifiers 110, 112. Reference signal 86 is passed through suitable phase shifters 96, 98, which may be formed from Allen Avionics Models V127050 (0–127 nsec) and VAR011 (0–11 nsec) switchable delay lines having 1 and 0.5 input resolution, i.e., 3.6 and 1.8 degree phase resolution at 10 MHz, respectively. A suitable phase shift is selected for the reference signal to discriminate selected fluorescence signals, as discussed above. Outputs 114 from the phase sensitive detectors 88, 89 are the phase resolved fluorescence outputs $v_{01}(t)$ and $v_{02}(t)$.

The dual-channel phase-sensitive detector shown in FIG. 4B may be used in two configurations to resolve fluorescence signals based on differences in lifetime. If only one photomultiplier tube (PMT) detector is used, inputs 84 to mixers 92, 94 are provided from a signal splitter (not shown) connected to PMT 78 (FIG. 3). Reference signal phase shifts $\phi_{ref1}$ 96 and $\phi_{ref2}$ 98 are then adjusted to resolve PMT detector 78 signals based on lifetime/phase differences as discussed above. It will be understood that the resolved signals may arise from two different fluorochromes, from a single fluorochrome with both bound and unbound components, one fluorochrome with emissions from a labeled cell and emission from Raman scattering, and the like. If both PMT detector 78 channels are used, i.e., a two-color detector, each PMT output is connected directly to a phase-sensitive detection channel and the channels are then used to enhance resolution of the two-color fluorescence emission signals.

A two-phase detector circuit (phase comparator) for making single decay time measurements is shown in FIG. 4C as a block diagram schematic. Quadrature phase hybrid module 118 may be an Anzac 2-32 MHz circuit and acts to output reference phase signal 86 with 0° and −90° phase shifts for input to separate phase-sensitive detectors 115, 117. Reference phase shifter 116, consisting of an Allen Avionics switchable delay line is used to initialize the two-phase measurement network using zero phase shift/lifetime signals from particles that have a zero lifetime ($\tau=0$). Phase-sensitive detector circuits 115, 117 include double balanced mixer/multipliers and amplifiers 120, 122; inverting amplifiers 124, 126; low-pass filters 128, 130; and amplifiers 132, 134, as discussed for FIG. 4B. The phase detector outputs are then input to ratio circuit 136, which outputs ratio signal 138 that is functionally related to the fluorescence decay lifetime. In another embodiment, the circuits shown in FIGS. 4B and 4C may have common phase sensitive detection electronics with switched input phase shifting and output processing electronics.

FIGS. 5A, 5B, 5C, 5D, and 5E present output results from the circuitry described above to demonstrate the capability to separate a single output signal formed from two fluorochromes having different lifetime decay characteristics. FIG. 5A depicts the single-parameter relative DNA content and total protein frequency distribution histograms individually recorded for propidium iodide (PI)- and FITC-stained normal CHO cell samples measured by phase-sensitive FCM. The output signals from PSD channels 88, 89 shown in FIG. 4B were maximized by adjustment of the respective reference phase shifts 96, 98

$$(\phi_{ref1}=\phi_{PI}=-43.2°; \phi_{ref2}=\phi_{FITC}=-12.6°)$$

as each sample was run independently. Peak 1 on the DNA distribution represents 2C diploid DNA content cells in $G_1$ phase prior to DNA replication and peak 2 represents 4C DNA content cells in $G_2$ and M phase following DNA replication. The cells contained between the two peaks are in S phase. The peak 2 to peak 1 modal fluorescence intensity ratio is 1.96 and the coefficient of variation (standard deviation divided by the mean) is 5.3%. The total protein distribution is broad, unimodal, and consistent with cells growing exponentially. Further, these results are the same as those obtained by conventional two-color fluorescence FCM.

The results of resolving the individual fluorescence signals from cells stained in combination with PI and FITC are shown in FIG. 5B. Using control samples stained with PI and FITC alone, the $\phi_{ref1}$ and $\phi_{ref2}$ reference signal phase shifts required to null FITC and PI signals in PSD channel No. 1 (88, FIG. 4B) and No. 2, (89, FIG. 4B) respectively, were determined to be −100.8° and 50.4°. These results agree closely with the theoretical values of −102.6° and 46.8°, as determined from the $-\pi/2+\phi_{FITC}$ and $\pi/2+\phi_{PI}$ phase shift expressions using the 3.6 and 15.0 nsec lifetimes measured for FITC and PI, respectively.

FIG. 5C shows the PSD outputs for extended passage (polyploid) CHO cells stained with PI and FITC in combination using the reference signal phase settings as determined for FIG. 5B. FIGS. 5D and 5E are the corresponding histograms and bivariate contour diagram determined from the resolved fluorescence signals. The relative DNA (peak 1) and total protein content frequency distribution histograms are both broadened by the resolution. Peak 1 is quite broad compared to the same peak in FIG. 5A and is indicative of nonspecific cell-staining or cells having slightly different $G_1$ phase DNA values. This is also evident in the number of S phase cells (peak 2). The bimodal total protein distribution shows two major regions of cells, small (Sm) cells of low mass centered about channel 50 and large (Lg) cells of higher mass (approximately twice the mass) centered about channel 95. When combined with the bimodal population of cells based on cell-mass measurement, cells contained in the broadened DNA content value of peak 1 are resolved into two distance polyploid cycling cell subpopulations, as clearly shown in the bivariate contour diagram (FIG. 5E).

The ability of the two-phase signal processing electronics (FIG. 4C) to determine directly decay lifetime is shown in FIGS. 6A, 6B, and 6C using a signal generator to simulate modulated fluorescence emission signals having selectable decay lifetimes. FIG. 6A shows that with the decay time set to zero nsec, i.e., −90° signal phase shift with respect to the PSD channel 115 (FIG. 4C) reference signal and 0° signal phase shift with respect to the PSD channel 117 reference signal, the histogram outputs from PSD channel 115 (proportional to $\sin \phi_s$) and channel 117 (proportional to $\cos \phi_s$) are zero and one, respectively. The corresponding ratio module 136 histogram output is zero. The decay time was next adjusted to 3.5 nsec, as shown in FIG. 6B, to simulate the fluorescence lifetime of a signal from FITC-labeled cells. In this test, the histogram output of PSD channel 115 increases from its initial value of zero and the output of PSD channel 117 decreases slightly from one. The corresponding histogram output value of ratio module 136 is slightly greater than 3.5 nsec. The final test results are shown in FIG. 6C. The simulated signal input decay lifetime was set to 15.0 nsec and the PSD channel 115, channel 117, and ratio module 136 histogram outputs were recorded. The resultant fluorescence lifetime measured at the ratio module output was between 15.0 and 16.0 nsec.

The foregoing description of the preferred embodiments of the invention have been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A phase-sensitive flow cytometer for resolving fluorescence emissions from fluorochrome labeled cells into two components, comprising:

flow cytometer means for providing a flow steam containing said labeled cells;

an excitation light for exciting said labeled cells to fluoresce in said flow stream;

modulation means for modulating said excitation light and generating a reference signal at a selected modulation frequency;

detector means for receiving fluorescence emission spectra from said labeled cells as a modulated fluorescence signal and outputting a modulated intensity signal functionally related to said fluorescence emission spectra from said labeled cells; and phase detector means for resolving said modulated intensity signal into two signal components, each functionally related to a different fluorescence decay lifetime of said fluorescent emission spectra.

2. A phase sensitive flow cytometer according to claim 1, wherein said phase detector means includes:

a phase shifter for phase shifting said reference signal an amount effective to null one of said two signal components in said modulated intensity signal; and a mixer for mixing said modulated intensity signal with said reference signal after said phase shifting to output a first signal functionally related one of said two signal components.

3. A phase sensitive flow cytometer for determining the fluorescence decay lifetime of a fluorescence emission, comprising:

flow cytometer means for providing a flow stream containing cells labeled with a fluorochrome;

an excitation light for exciting said fluorochrome to fluoresce in said flow stream;

modulation means for modulating said excitation light and generating a reference signal at a selected modulation frequency;

detector means for receiving a fluorescence emission spectra from said fluorochrome as a modulated fluorescence signal and outputting a modulated intensity signal functionally related to said fluorescence emission spectra from said fluorochrome; and phase detector means for inputting said modulated intensity signal and outputting two phase shifted signals whose ratio is functionally related to said fluorescence lifetime.

4. A phase sensitive flow cytometer according to claim 3, wherein said phase detector comprises:

a quadrature phase circuit for outputting said reference signal that is phase shifted by 0° and by 90° to form two phase shifted reference signals;

two phase sensitive detector means for mixing said modulated fluorescence signal from said fluorochrome with one of each said two phase shifted reference signals and outputting two quadrature signals; and means for forming the ratio of said two quadrature signals and outputting a signal functionally related to the fluorescence lifetime of said fluorochrome.

* * * * *